United States Patent [19]
Amiri et al.

[11] Patent Number: 5,656,273
[45] Date of Patent: Aug. 12, 1997

[54] METHOD OF TREATMENT OF PARASITIC INFECTION USING IGE ANTAGONISTS

[75] Inventors: Payman Amiri, San Francisco, Calif.; Mary Haak-Frendscho, Fitchburg, Wis.; Paula M. Jardieu, Berkeley, Calif.

[73] Assignee: Genentech, Inc., South San Francisco, Calif.

[21] Appl. No.: 422,748

[22] Filed: Apr. 14, 1995

Related U.S. Application Data

[63] Continuation of Ser. No. 184,083, Jan. 18, 1994, abandoned.
[51] Int. Cl.$^6$ .................................................. A61K 39/395
[52] U.S. Cl. .................................. 424/158.1; 424/184.1; 530/388.1; 530/388.25; 530/389.3; 530/387.1
[58] Field of Search ........................... 424/158.1, 184.1; 530/388.1, 388.25, 389.3, 387.1; 435/240.27, 172.2, 70.21

[56] References Cited

U.S. PATENT DOCUMENTS

| | | |
|---|---|---|
| 4,714,759 | 12/1987 | Whitaker, Jr. . |
| 4,940,782 | 7/1990 | Rup et al. . |
| 4,946,788 | 8/1990 | Delespesse . |
| 4,962,035 | 10/1990 | Leder et al. . |
| 5,091,313 | 2/1992 | Chang . |
| 5,252,467 | 10/1993 | Chang . |

FOREIGN PATENT DOCUMENTS

| | | |
|---|---|---|
| 476226 | 3/1992 | European Pat. Off. . |
| WO 89/06138 | 7/1989 | WIPO . |
| WO 93/04173 | 3/1993 | WIPO . |
| WO 93/05810 | 4/1993 | WIPO . |

OTHER PUBLICATIONS

Amiri et al., "Anti-immunoglobulin E Treatment Decreases Worm Burden and Egg Production in Schistosoma mansoni-infected Normal and Interferon γ Knockout Mice" *J. of Experimental Medicine* 180: 43–51 (Jul. 1994).

Amiri et al., "Tumor necrosis factor α restores granulomas and induces parasite egg-laying in schistosome-infected SCID mice" *Nature* 356: 604–607 (Apr. 16, 1992).

Auriault et al., "Rat IgE directed against schistosomula released products is cytotoxic for Schistosoma mansoni schistosomula in vitro" *European Journal of Immunology* 14(2): 132–138 (Feb. 1984).

Bach et al., "Safety and efficacy of therapeutic monoclonal antibodies in clinical therapy" *Immunology Today* 14(9): 421–425 (1993).

Baird et al., "Interaction of IgE with Its High-Affinity Receptor" *International Archives of Allergy & Applied Immunology* 88: 23–28 (1989).

Bazin et al., "Effect of neonatal injection of anti-μ antibodies on immunity to schistosomes (*S. mansoni*) in the rat" *Journal of Immunology* 124(5): 2373–2377 (1980).

Boctor et al., "IgG subclasses in human chronic schistosomiasis: over-production of schistosome-specific and non-specific IgG4" *Clinical & Experimental Immunology* 82(3): 574–578 (1990).

Borrebaeck, Carl A.K., "Strategy for the production of human monoclonal antibodies using in vitro activated B cells" *J. Immunol. Methods* 123: 157–165 (1989).

Capron et al., "Antibody-dependent cell-mediated cytotoxicity against parasites" *Progress in Allergy* 31: 234–267 (1982).

Capron et al., "Effector and regulatory mechanisms in immunity to schistosomes: a heuristic view" *Annual Review of Immunology* 3: 455–476 (1985).

Capron et al., "Role of IgE receptors in effector function of human eosinophils" *Journal of Immunology* 132(1): 462–468 (1984).

Capron et al., "Specific IgE antibodies in immune adherence of normal macrophages to Schistosoma mansoni schistosomules" *Nature* 253(5491): 474–475 (1975).

Dunne et al., "Immunity after treatment of human schistosomiasis: association between IgE antibodies to adult worm antigens and resistance to reinfection" *European Journal of Immunology* 22(6):1483–1494 (1992).

Finkelman et al., "Regulation and biological function of helminth-induced cytokine responses" *Immunology Today* 12(3): A62–A66 (1991).

Flores-Romo et al., "Inhibition of an in vivo antigen-specific IgE response by antibodies to CD23" *Science* 261(5124): 1038–1041 (1993).

Gordon et al., "Mast cells as a source of both preformed and immunologically inducible TNF-α/cachectin" *Nature* 346: 274–276 (Jul. 19, 1990).

Hagan et al., "Human IgE, IgG4 and resistance to reinfection with *Schistosoma haematobium*" *Nature* 349 (6306): 243–245 (1991).

Harris et al., "Therapeutic antibodies—the coming of age" *TIBTECH* 11: 42–44 (Feb. 1993).

Hook et al., "Monoclonal antibodies to human IgE" *Federation Proceedings* 40(3): 4177 (1994).

Joseph et al., "Characteristics of macrophage cytotoxicity induced by IgE immune complexes" *Cellular Immunology* 34(2): 247–258 (1977).

Joseph et al., "A new function for platelets: IgE-dependent killing of schistosomes" *Nature* 303(5920): 810–812 (1983).

Kigoni et al., "IgE antibody and resistance to infection. II. Effect of IgE suppression on the early and late skin reaction and resistance of rats to *Schistosoma mansoni* infection" *European Journal of Immunology* 16(6): 589–595 (1986).

Klein, "The IgE-aosinophil system" *Immunology*, Blackwell Scientific Publications p. 415 (1990).

(List continued on next page.)

*Primary Examiner*—Toni R. Scheiner
*Attorney, Agent, or Firm*—Renee A. Fitts; Robin L. Teskin; Craig G. Svoboda

[57] ABSTRACT

This invention concerns a method for the prevention and treatment of parasitic infection by administering an IgE antagonists. The invention further concerns pharmaceutical compositions and bispecific molecules useful in such method.

29 Claims, 5 Drawing Sheets

OTHER PUBLICATIONS

Kolbinger et al., "A Humanized Antibody for the Treatment of Allergy" *Protein Engineering* (Abstract, top left), Oxford, GB 6(Suppl.):90 (1993).

Liu et al., "Fusion between transcription factor CBF β/PEBP2 β and a myosin heavy chain in acute myeloid leukemia" *Science* 261(5124): 1041–1044 (1993).

Lynch et al., "Effect of anthelmintic treatment on the allergic reactivity of children in a tropical slum" *J. Allergy Clin. Immunol.* (see Abstract) 92(3): 404–411 (Sep. 1993).

Marshall et al., "Accelerated elimination of N. brasiliensis from the small intestine after auto–anti–IgE induction" *Immunology* 60: 303–308 (1987).

Moqbel et al., "Enhanced granulocyte cytotoxicity by mediators derived from anti–IgE–stimulated human leucocytes" *Immunology* 59(1): 87–93 (1986).

Moqbel et al., "Enhancement of human eosinophil–and neutrophil–mediated killing of schistosomula of *Schistosoma mansoni* by reversed type (IgE–mediated) anaphylaxis, in vitro" *Clinical & Experimental Immunology* 59(3): 577–586 (1985).

Moqbel et al., "Release of leukotriene $C_4$ ($LTC_4$) from human eosinophils following adherence to Ig IgG–coated schistosomula of *Schistosoma mansoni*" *Immunology* 69(3): 435–442 (1990).

Mosmann et al., "Th1 and TH2 cells: different patterns of lymphokine secretion lead to different functional properties" *Annual Review of Immunology* 7: 145–173 (1989).

Ohkawara et al., "Human Lung Mast Cells and Pulmonary Macrophages Produce Tumor Necrosis Factor–$\alpha$ in Sensitized Lung Tissue after IgE Receptor Triggering" *Am. J. Respir. Cell Mol. Biol.* 7: 385–392 (1992).

Osband et al., "Problems in the investigational study and clinical use of cancer immunotherapy" *Immunology Today* 11(6): 193–195 (1990).

Owhashi et al., "Granulomatous Response in Selective IgE–Deficient SJA/9 Mice Infected with *Schistosoma japonicum*" *Int. Arch. Allergy Appl. Immunol.* 90: 310–312 (1989).

Paul, W., "Interleukin–4: a prototypic immunoregulatory lymphokine" *Blood* 77(9): 1859–1870 (1991).

Presta et al., "Humanization of an Antibody Directed Against IgE" *J. Immunol.* 151(5): 2623–2632 (Sep. 1, 1993).

Rihet et al., "Evidence for an association between human resistance to *Schistosoma mansoni* and high anti–larval IgE levels" *European Journal of Immunology* 21(11): 2679–2686 (1991).

Scott et al., "Role of cytokines and CD4+T–cell subsets in the regulation of parasite immunity and disease" *Immunological Reviews* 112: 161–182 (1989).

Sher et al., "Ablation of eosinophil and IgE responses with anti–IL–5 and anti–IL–4 antibodies fails to affect immunity against *Schistosoma mansoni* in the mouse" *Journal of Immunology* 145(11): 3911–3916 (1990).

Sher et al., "Regulation of immunity to parasites by T cells and T cell–derived cytokines" *Annual Review of Immunology* 10: 385–409 (1992).

Sher, Alan, "Parasitizing the cytokine system" *Nature* 356: 565–566 (Apr. 16, 1992).

Velge–Roussel et al., "Protective effects of anti–antiidiotypic IgE antibodies obtained from an IgE monoclonal antibody specific for a 26–kilodalton *Schistosoma mansoni* antigen" *Journal of Immunology* 142(7): 2527–2532 (1989).

Vella et al., "CD4+ Th2 Response Induced by *Schistosoma mansoni* Eggs Develops Rapidly, Through an Early, Transient, Th0–Like Stage" *J. of Immunology* 148(7): 2283–2290 (Apr. 1, 1992).

Verwaerde et al., "Role of serine proteases of *Schistosoma mansoni* in the regulation of IgE synthesis" *Scandinavian Journal of Immunology* 24(5): 509–516 (1986).

Vignali et al., "Immunity to *Schistosoma mansoni* in vivo: contradiction or clarification?" *Immunology Today* 10(12): 410–416 (1989).

Warren, "Schistosomes and other trematodes" *Medical Microbiology* 103:1077, 1080–1083 (1986).

Weltman eta l., "An analysis of allergy, immunoglobulin E, and diagnostic skin tests in schistosomiasis" *Parasite Immunology* 3(2): 157–163 (1981).

Queen et al. PNAS USA 86:10029–10023, 1989.

METHOD OF TREATMENT OF PARASITIC INFECTION USING IGE ANTAGONISTS

This is a continuation of application Ser. No. 08/184,083 filed on Jan. 18, 1994, now abandoned, which application is incorporated herein by reference and to which application priority is claimed under 35 USC §120.

FIELD OF THE INVENTION

This invention relates to methods for preventing or treating parasitic infection. Particularly, according to this invention, an IgE antagonist is administered to a patient having or at risk of having a parasitic infection, to eliminate or render undetectable the patient's IgE levels during the course of the infection.

DESCRIPTION OF BACKGROUND AND RELATED ART

Elevated IgE antibody production is a hallmark of infection with parasitic helminths, including Schistosoma mansoni (Finkelman, F. D., et al., Immun. Today 12:462–466 (1991)). This IgE response is commonly considered an essential component of the host defense against metazoan parasites (Capron, A. et al., Nature 253:474–475 (1975); Capron, A., et al., Prog. Allergy 31:234–267 (1982); Joseph, M., et al., Nature 303:810–812 (1983)). Numerous studies have supported this hypothesis: B cell depletion prevents development of immunity (Bazin, H., et al., J. Immun. 124:2373–2377 (1980)); effective immunity can be adoptively transferred by IgE antibodies (Capron, A. et al., Ann. Rev. Immun. 3:455–476 (1985); Vignali, D. A. A. et al., Immun. Today 10:410–416 (1989)); IgE can directly mediate resistance through eosinophil, macrophage, and platelet-mediated cytotoxicity (Joseph, M., et al., Nature 303:810–812 (1983); Capron, M. et al., J. Immun. 132:462–468 (1984); Auriault, C. et al., Eur. J. Immun. 14:132–138 (1984)). In addition, recent epidemiological reports demonstrate a correlation between high schistosoma-specific IgE antibody levels and resistance to reinfection (Hagan, P. et al., Nature 349:243–2445 (1991); Rihet, P. et al., Eur. J. Immunol. 21:2679–2686 (1991); Dunne, D. W. et al., Eur. J. Immun. 22:1483–1494 (1992). Most of the studies which have been undertaken to investigate the role of IgE in parasite immunity, have employed systems in which IgE is deficient as a result of genetic mutation(s) or via elimination of the pluripotent lymphokine IL-4.

Surprisingly, the present inventors have discovered that elimination of IgE with an IgE antagonist, as measured by reduction of IgE to an undetectable level in an ELISA assay, resulted in decreased worm burden, decreased egg production, and decreased heptospenomegaly in murine schistosomiasis.

Antagonists of IgE in the form of receptors, anti-IgE antibodies, binding factors, or fragments thereof have been disclosed in the art. U.S. Pat. No. 4,962,035 discloses DNA encoding the alpha-subunit of the mast cell IgE receptor or an IgE binding fragment thereof. Hook et al. (Federation Proceedings Vol. 40, No. 3, Abstract #4177) disclose monoclonal antibodies, of which one type is anti-idiotypic, a second type binds to common IgE determinants, and a third type is directed towards determinants hidden when IgE is on the basophil surface.

U.S. Pat. No. 4,940,782, discloses monoclonal antibodies which react with IgE when it is unbound and thereby inhibit IgE binding to mast cells, and react with IgE when it is bound to the B-cell FcE receptor, but do not bind with IgE when it is bound to the mast cell FcE receptor, nor block the binding of IgE to the B-cell receptor.

U.S. Pat. No. 4,946,788 discloses a purified IgE binding factor and fragments thereof, and monoclonal antibodies which react with IgE binding factor and lymphocyte cellular receptors for IgE, and derivatives thereof.

U.S. Pat. No. 5,091,313 discloses antigenic epitopes associated with the extracellular segment of the domain which anchors immunoglobulins to the B cell membrane. The epitopes recognized are present on IgE-bearing B cells but not basophils or in the secreted, soluble form of IgE. U.S. Pat. No. 5,252,467 discloses a method for producing antibodies specific for such antigenic epitopes. U.S. Pat. No. 5,231,026 discloses DNA encoding murine-human antibodies specific for such antigenic epitopes.

WO 89/06138 discloses unique antigenic determinants of IgE present on IgE bearing B-cells but not basophils. One class of these epitopes is at or near the FceR binding site on IgE, while another class of associated with the extracellular segment of the domain of ε chains which anchor IgE to the B cell membrane.

U.S. Pat. No. 4,714,759 discloses an immunotoxin in the form of an antibody or an antibody fragment coupled to a toxin to treat allergy.

Presta et al. (J. Immunol. 151:2623–2632 (1993)) disclose a humanized anti-IgE that prevents the binding of free IgE to FceRI but does not bind to FceRi-bound IgE. Copending WO93/04173 discloses polypeptides which bind differentially to the high- and low-affinity IgE receptors.

Flores-Romo et al. (Science 261:1038–1041 (1993)) disclose inhibition of an in vivo antigen-specific IgE response by antibodies to CD23.

Thus, it is an object of this invention to provide a method for preventing or treating parasitic infection by administering an IgE antagonist to a patient.

SUMMARY OF THE INVENTION

One aspect of the invention is a method of treating infection of a patient by a parasite comprising administration of a therapeutically effective amount of an IgE antagonist to the patient.

Another aspect of the invention is a method of reducing the number of eggs or adult worms in a patient infected by a parasite comprising administration of a therapeutically effective amount of an IgE antagonist to the patient.

Another aspect of the invention is a method of reducing hepatosplenomegaly in a patient infected by a parasite comprising administration of a therapeutically effective amount of an IgE antagonist to the patient.

(240 μg total anti-IgE mAb). Total serum IgE was determined by ELISA. Polyclonal rabbit anti-mouse IgE (Genentech, Inc.) was diluted to 2 μg/ml in 0.05M $Na_2CO_3$ buffer, pH 9.6, and coated onto flat-bottomed microtiter plates. The amount of murine IgE that bound to the anti-mouse IgE was detected using biotinylated IgE receptor I-IgG immunoadhesin (Haak-Frendscho, M. et al., *J. Immun.* 151:351–358 (1993)). Assays were developed using horseradish peroxidase conjugated to streptavidin (Zymed).

Figure 1:
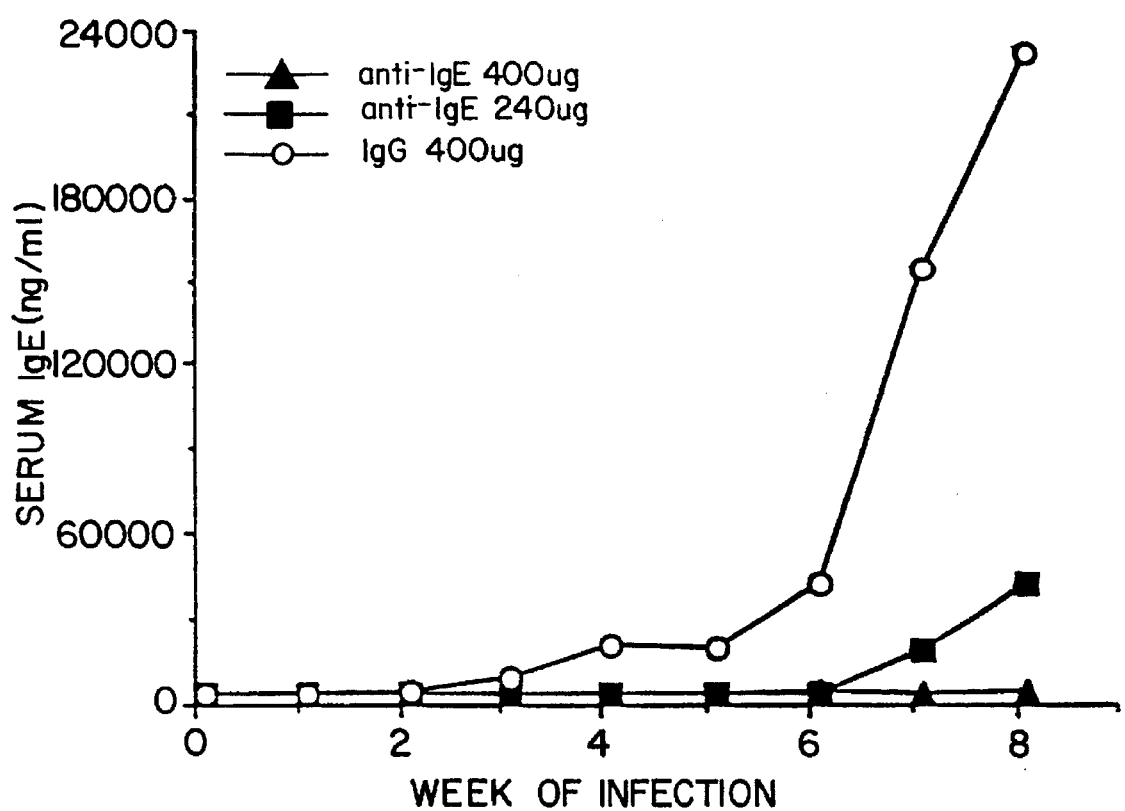
FIG. 1 is a graph depicting the effects of anti-IgE monoclonal antibodies (mAb) on serum IgE levels. BALB/c mice, stated by supplier to be free of adventitious viruses, were housed under microisolator caps in a quarantine room. Once acclimated to the facility, the 6–8 week old mice were treated intravenously (iv) with either 100 μg anti-IgE mAb (R35-92, rat IgG1; Pharmingen) or an isotype matched control antibody (rat $IgG_{1\kappa}$; Pharmingen). The following day, mice were infected by body surface exposure to 90 cercariae of S. mansoni shed from infected Biompharlaria glabrata snails. At weekly intervals, mice were bled, then retreated in vivo with 20 μg mAb at 1, 2, 3, 4, and 5 weeks, and with 100 μg at weeks 6 and 7 (400 μg total anti-IgE mAb), or with 20 μgmAb anti-IgE mAb at weeks 6 and 7
Figure 2A:
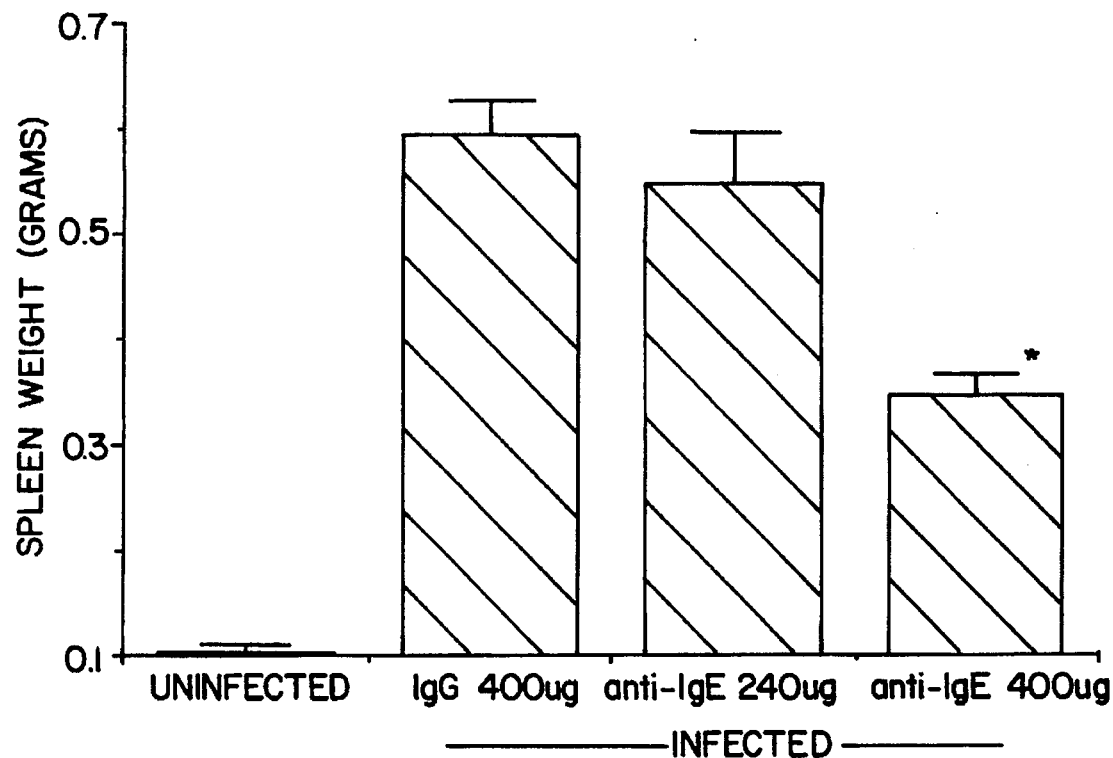
Figure 2B:
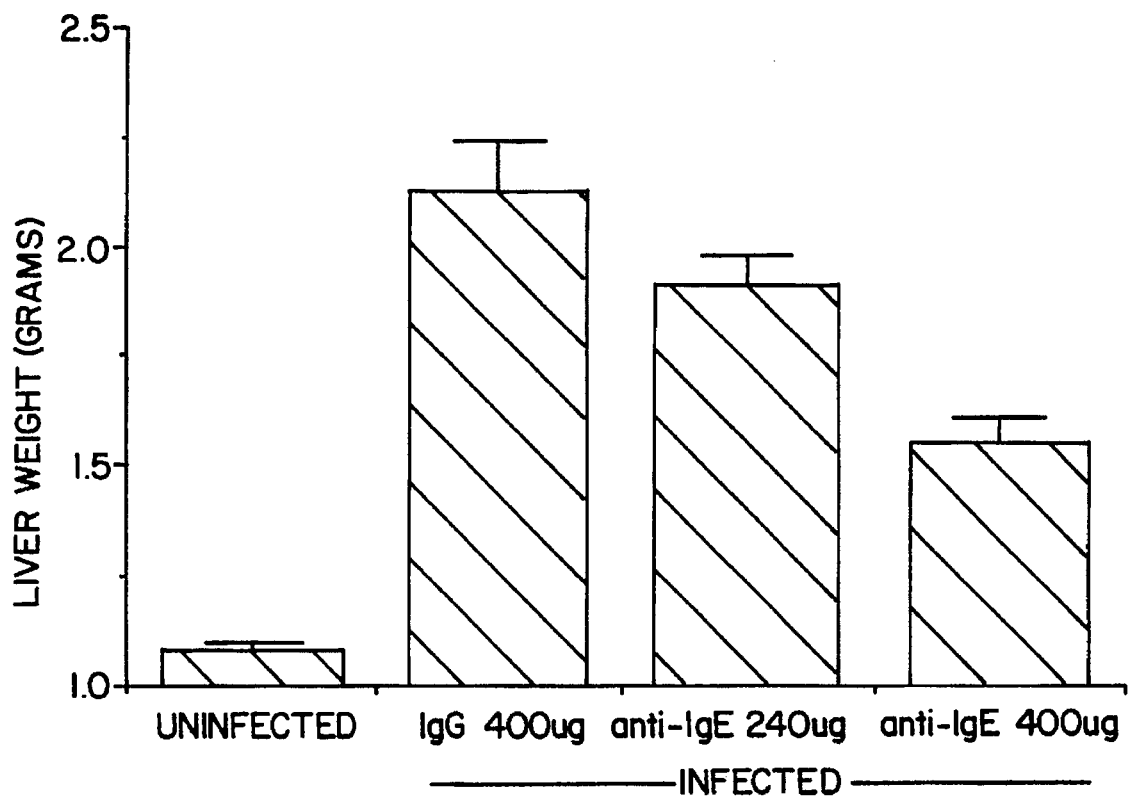

FIGS. 2A and 2B are graphs depicting the effect of anti-IgE on spleen weight (2A) and liver weight (2B). Spleen and liver weight, as a gross indication of cellular infiltration and inflammation, were determined eight weeks after infection with cercariae as described in the legend to FIG. 1. Results are expressed as the mean (n=7–12/group) wet weight±standard deviation.

FIGS. 3(A–D) is a photograph depicting the histopathology of livers and spleens from infected mice. To evaluate histopathology, spleens and livers were removed from mice treated with high dose anti-IgE or control IgG, eight weeks after infection with cercariae as described in the legend to FIG. 1. Organs were fixed in 10% buffered formalin, embedded in paraffin, sectioned, then stained with hematoxylin and eosin. Livers from control mice contained multiple large coalescing foci of granulomas predominately composed of macrophages and eosinophils 3(A). Livers of anti-IgE mAb treated animals had fewer eggs and therefore fewer granulomas 3(B). The histologic characteristics, notably the presence of macrophages and numerous eosinophils, were similar in both groups. However, the granulomas of the anti-IgE treated group 3(D) did appear to have less fibrosis than those from control mice 3(C).

Figure 4:
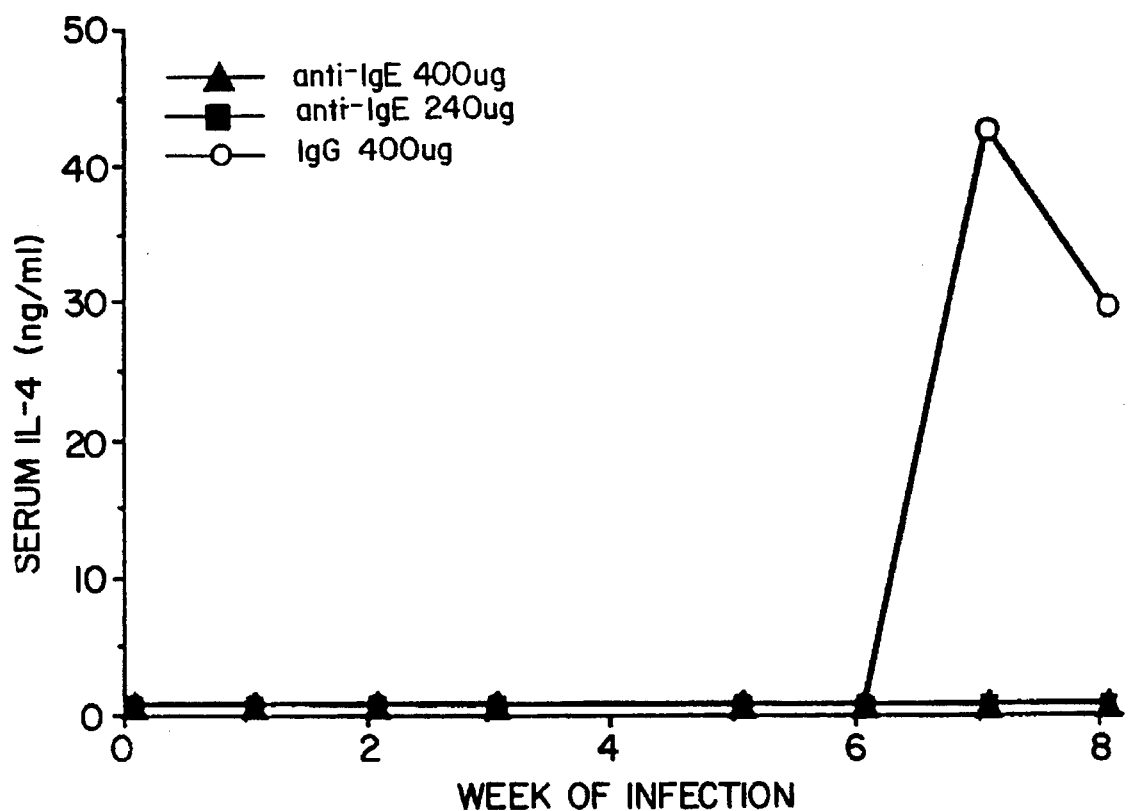

FIG. 4 is a graph depicting the effect of anti-IgE on serum IL-4. Serum IL-4 was determined by ELISA using 1 μg/ml anti-mouse IL-4 mAb (BVD4-1D11, rat $IgG_{2b}$; Pharmingen) in 0.05M $Na_2CO_3$, pH 9.6, coated onto flat-bottomed microtiter plates. IL-4 was detected with biotin-conjugated anti-mouse IL-4 (BVD6-24G2, rat $IgG_1$; Pharmingen) and developed with horseradish peroxidase-streptavidin (Zymed).

Figure 5:
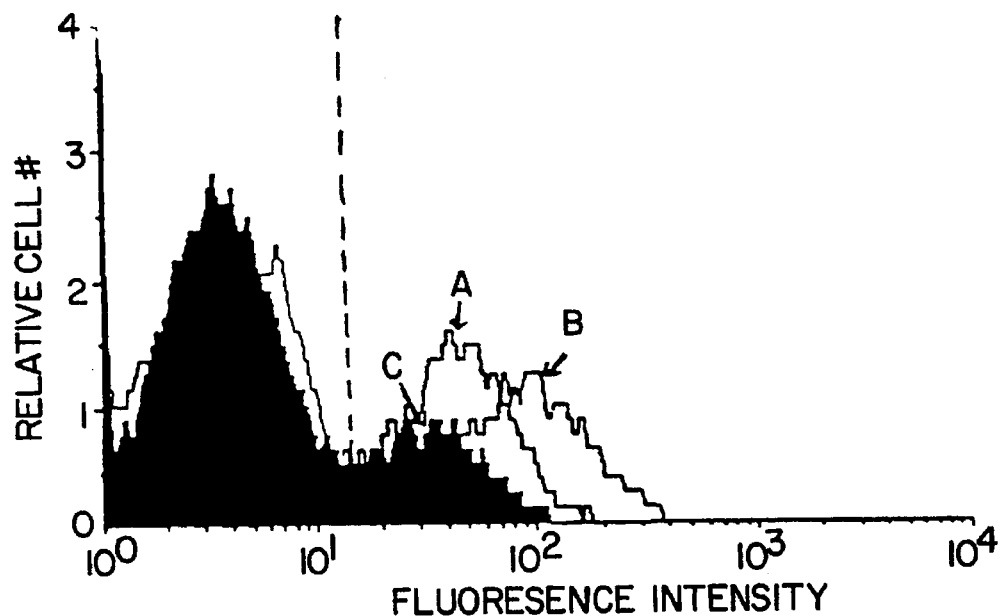

FIG. 5 is a graph depicting CD23 expression on B cells. Spleens were removed from anti-IgE mAb and control antibody treated mice after eight weeks of infection with *S. mansoni*. Their cells were dispersed with frosted glass slides, washed with phosphate buffered saline (PBS) containing 1% bovine serum albumin (BSA) and 0.01% sodium azide, then stained with appropriate dilutions of monoclonals recognizing CD45R (RA3–6B2, Red6 13-conjugated rat $IgG_{2a}$; GIBCO) and CD23 (B3B4, FITC-conjugated rat $IgG_{2a}$; Pharmingen). Cells were analyzed using a FACScan gating on the lymphocyte population. Splenocytes from uninfected mice were used for reference for B cell expression of CD23 (a). Cells from mice treated with control antibody showed a marked upregulation of CD23 (b) expression in response to *Schistosoma* infection. In contrast, CD23 (c) expression on spleen cells was reduced as a result of anti-IgE mAb treatment.

DETAILED DESCRIPTION OF THE PREFERRED EMBODIMENTS

A. DEFINITIONS

The term "IgE antagonist" as used herein refers to a substance which inhibits the biological activity of IgE. Such antagonists include but are not limited to anti-IgE antibodies, IgE receptors, anti-IgE receptor antibodies, variants of IgE antibodies, ligands for the IgE receptors, and fragments thereof. Antibody antagonists may be of the IgA, IgD, IgG, IgE, or IgM class. In some embodiments of the invention, the antibody antagonist may be bispecific, i.e., comprise an antigen binding site and an amino acid sequence capable of binding a target involved in the initiation or development of parasitic infection. Variant IgE antibodies typically have amino acid substitutions or deletions at one or more amino acid residues. Ligands for IgE receptors include but are not limited to IgE and anti-receptor antibodies, and fragments thereof capable of binding to the receptors, including amino acid substitution and deletion variants, and cyclized variants.

In general, in some embodiments of the invention, IgE antagonists act by blocking the binding of IgE to its receptors on B cells, mast cells, or basophils, either by blocking the binding site on the IgE molecule or blocking its receptors. Additionally, in some embodiments of the invention, IgE antagonists act by binding soluble IgE and thereby removing it from circulation. The IgE antagonists of the invention can also act by binding to IgE on B cells, thereby eliminating clonal populations of B cells. The IgE antagonists of the instant invention can also act by inhibiting IgE production. Preferably, the IgE antagonists of the instant invention do not result in histamine release from mast cells or basophils.

The term "therapeutic amount" as used herein denotes an amount that prevents or ameliorates symptoms of a disorder or responsive pathologic physiological condition.

"Polypeptide" as used herein refers generally to peptides and proteins having at least about two amino acids.

B. GENERAL METHODS

The IgE antagonists of the instant invention can be used to treat infection by parasitic helminths, including nematodes, trematodes, and cestodes, and other parasites which are associated with elevated IgE levels.

IgE antagonists and methods for designing and producing them are known in the art (see *Description of the Background and Related Art*). When the IgE antagonist is an antibody, it can be any type of immunoglobulin, such as IgG, IgA, IgM, IgD, and IgE, including polyclonal and monoclonal forms of such antibodies.

Polyclonal antibodies to IgE generally are raised in animals by multiple subcutaneous (sc) or intraperitoneal (ip) injections of IgE and an adjuvant. It can be useful to conjugate IGE or a fragment containing the target amino acid sequence from the Fc region of IGE to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals ordinarily are immunized against the cells or immunogenic conjugates or derivatives by combining 1 mg or 1 μg of IgE with Freund's complete adjuvant and injecting the solution intradermally at multiple sites. One month later the animals are boosted with ⅕ to ⅒ the original amount of conjugate in Freund's complete adjuvant by subcutaneous injection at multiple sites. Seven to 14 days later, animals are bled and the serum is assayed for anti-IgE titer. Animals are boosted until the titer plateaus. Preferably, the animal is boosted with a conjugate of the same IgE, but conjugated to a different protein and/or through a different cross-linking agent. Conjugates also can be made in recombinant cell culture as protein fusions. Also, aggregating agents such as alum can be used to enhance the immune response.

Monoclonal antibodies are prepared by recovering spleen cells from immunized animals and immortalizing the cells in conventional fashion, e.g. by fusion with myeloma cells or by Epstein-Barr (EB)-virus transformation and screening for clones expressing the desired antibody. The hybridoma technique described originally by Koehler and Milstein, *Eur. J. Immunol.*, 6: 511 (1976) and also described by Hammerling et al., in: *Monoclonal Antibodies and T-Cell Hybridomas*, Elsevier, N.Y., pp. 563–681 (1981) has been widely applied to produce hybrid cell lines that secrete high levels of monoclonal antibodies against many specific antigens.

The hybrid cell lines can be maintained in vitro in cell culture media. The cell lines producing the antibodies can be selected and/or maintained in a composition comprising the continuous cell line in hypoxanthine-aminopterin thymidine (HAT) medium. In fact, once the hybridoma cell line is established, it can be maintained on a variety of nutritionally adequate media. Moreover, the hybrid cell lines can be stored and preserved in any number of conventional ways, including freezing and storage under liquid nitrogen. Frozen cell lines can be revived and cultured indefinitely with resumed synthesis and secretion of monoclonal antibody.

The secreted antibody is recovered from tissue culture supernatant by conventional methods such as precipitation, ion-exchange chromatography, affinity chromatography, or the like. The antibodies described herein are also recovered from hybridoma cell cultures by conventional methods for purification of IgG or IgM, as the case may be, that heretofore have been used to purify these immunoglobulins from pooled plasma, e.g., ethanol or polyethylene glycol precipitation procedures. The purified antibodies are sterile-filtered.

While routinely mouse monoclonal antibodies are used, the invention is not so limited; in fact, human antibodies can be used. Such antibodies can be obtained, for example, by using human hybridomas (Cote et al., *Monoclonal Antibodies and Cancer Therapy*, Alan R. Liss, p. 77 (1985)). In fact, according to the invention, techniques developed for the production of chimeric antibodies (Cabilly et al., U.S. Pat. No. 4,816,567, Morrison et al., *Proc. Natl. Acad. Sci.*, 81: 6851 (1984); Boulianne et al., *Nature*, 312: 643–646 (1984); Neuberger et al., *Nature*, 312:604 (1984); Neuberger et al., *Nature*, 314:268–270 (1985); Takeda et al., *Nature*, 314:452 (1985); EP 184,187; EP 171,496; EP 173,494; PCT WO 86/01533; Shaw et al., *J. Nat. Canc. Inst.*, 80: 1553–1559 (1988); Morrison, *Science*, 229: 1202–1207 (1985); Oi et al., *BioTechniques*, 4: 214 (1986)) by coupling an animal antigen-binding variable domain to a human constant domain can be used; such antibodies are within the scope of this invention. The term "chimeric" antibody is used herein to describe a polypeptide comprising at least the antigen binding portion of an antibody molecule linked to at least part of another protein (typically an immunoglobulin constant domain).

In one embodiment, such chimeric antibodies contain about one third rodent (or other non-human species) sequence and thus are capable of eliciting a significant anti-globulin response in humans. For example, in the case of the murine anti-CD3 antibody OKT3, much of the resulting anti-globulin response is directed against the variable region rather than the constant region (Jaffers et al., *Transplantation*, 41: 572–578 (1986)).

Humanized antibodies are used to reduce or eliminate any anti-globulin immune response in humans. In practice, humanized antibodies are typically human antibodies in which some amino acid residues from the complementarity determining regions (CDRs), the hypervariable regions in the variable domains which are directly involved with formation of the antigen-binding site, and possibly some amino acids from the framework regions (FRs), the regions of sequence that are somewhat conserved within the variable domains, are substituted by residues from analogous sites in rodent antibodies. The construction of humanized antibodies is described in Riechmann et al., *Nature*, 332:323–327 (1988), Queen et al., *Proc. Natl. Acad. Sci. USA*, 86: 10029–10033 (1989), Co et al., *Proc. Natl. Acad. Sci. USA*, 88:2869–2873 (1991), Gorman et al., *Proc. Natl. Acad. Sci.*, 88: 4181–4185 (1991), Daugherty et al., *Nucleic Acids Res.*, 19: 2471–2476 (1991), Brown et al., *Proc. Natl. Acad. Sci. USA*, 88: 2663–2667 (1991), Junghans et al., *Cancer Res.*, 50:1495–1502 (1990), Fendly et al., *Cancer Res.*, 50: 1550–1558 (1990) and in PCT applications WO 89/06692 and WO 92/22653.

In some cases, substituting CDRs from rodent antibodies for the human CDRs in human frameworks is sufficient to transfer high antigen binding affinity (Jones et al., *Nature*, 321: 522–525 (1986); Verhoeyen et al., *Science*, 239: 1534–1536 (1988)) whereas in other cases it is necessary to additionally replace one (Riechmann et al., supra) or several (Queen et al., supra) FR residues. See also Co et al., supra.

The invention also encompasses the use of human antibodies produced in transgenic animals. In this system, DNA encoding the antibody of interest is isolated and stably incorporated into the germ line of an animal host. The antibody is produced by the animal and harvested from the animal's blood or other body fluid. Alternatively, a cell line that expresses the desired antibody can be isolated from the animal host and used to produce the antibody in vitro, and the antibody can be harvested from the cell culture by standard methods.

Anti-IgE antibody fragments can also be used in the methods of the invention. Any fragment of an anti-IgE antibody capable of blocking or disrupting IgE interaction with its receptor is suitable for use herein.

Suitable anti-IgE antibody fragments can be obtained by screening combinatorial variable domain libraries for DNA capable of expressing the desired antibody fragments. These techniques for creating recombinant DNA versions of the antigen-binding regions of antibody molecules (known as F(ab) fragments), which bypass the Generation of monoclonal antibodies, are encompassed within the practice of this invention. One typically extracts antibody-specific messenger RNA molecules from immune system cells taken from an immunized animal, transcribes these into complementary DNA (cDNA), and clones the cDNA into a bacterial expression system. One can rapidly generate and screen great numbers of functional F(ab) fragments for those that bind the antigen of interest. Such IgE-binding molecules (F(ab) fragments with specificity for the IgE protein) are specifically encompassed within the term "antibody" as it is defined, discussed, and claimed herein.

In a further embodiment of the invention, soluble IgE receptor can be used as the IgE antagonist. Soluble receptors suitable for use herein include, for example, molecules comprising the IgE binding site in the extracellular domain (exodomain) of the FceRI $\alpha$ chain. The $\alpha$ chain of FceRI can be genetically modified such that the exodomain is secreted as a soluble protein in a recombinant expression system according to the method of Blank et al., *J. Biol. Chem.*, 266:2639–2646 (1991) or Qu et al., *J. Exp. Med.*, 167: 1195.

The invention also encompasses the use of IgE-binding peptides in addition to anti-IgE antibodies and soluble receptor. Any IgE-binding peptide capable of disrupting or blocking the interaction between IgE and its receptors is suitable for use herein.

In addition to IgE antagonists which interfere with IgE/receptor interaction by binding to IgE, such as anti-IgE antibodies, fragments thereof, soluble IgE receptor and other IgE-binding peptides described above, the invention encompasses the use of IgE antagonists which disrupt IgE/receptor interaction by competing with IgE for binding to its receptor, thereby lowering the available IgE receptor.

IgE variants are an example of a receptor-binding competitor that is suitable for use in the methods of the invention. IgE variants are forms of IgE possessing an alteration, such as an amino acid substitution or substitutions and/or an amino acid deletion or deletions, wherein the altered IgE molecule is capable of competing with IgE for binding to its receptors.

Fragments of IgE variants are also suitable for use herein. Any fragment of an IgE variant capable of competing with IgE for binding to its receptors can be used in the methods of the invention.

The invention also encompasses the use of receptor-binding peptides in addition to IgE variants and fragments thereof. Any IgE receptor-binding peptide capable of disrupting or blocking the interaction between IgE and its receptors is suitable for use herein.

Practice of the invention is not limited to the use of peptide IgE antagonists. Any compound capable of functioning as an IgE antagonist is suitable for use in the methods of the invention, including non-proteinaceous small molecule compounds.

The amount of IgE antagonist delivered to the patient to be used in therapy will be formulated and dosages established in a fashion consistent with good medical practice taking into account the disorder to be treated, the condition of the individual patient, the site of delivery, the method of administration and other factors known to practitioners. Similarly, the dose of the IgE antagonist administered will be dependent upon the properties of the IgE antagonist employed, e.g. its binding activity and in vivo plasma half-life, the concentration of the IgE antagonist in the formulation, the administration route, the site and rate of dosage, the clinical tolerance of the patient involved, the pathological condition afflicting the patient and the like, as is well within the skill of the physician.

Typically the IgE antagonists are administered subcutaneously or intravenously about once a week for about two months, in amounts of about 2 to 3 mg/kg. Typically, when anti-IgE antibody is used, sufficient antibody is administered so that its concentration is about twice the serum IgE level. Antagonists of the invention are administered by intravenous intrapulmonary, intraperitoneal subcutaneous or other suitable routes.

It is envisioned that injections (intramuscular or subcutaneous) will be the primary route for therapeutic administration of the IgE antagonist of this invention, although intravenous delivery, or delivery through catheter or other surgical tubing is also used. Alternative routes include suspensions, tablets, capsules and the like for oral administration, commercially available nebulizers for liquid formulations, and inhalation of lyophilized or aerosolized microcapsules, and suppositories for rectal or vaginal administration. Liquid formulations can be utilized after reconstitution from powder formulations.

Additional pharmaceutical methods may be employed to control the duration of action of the antagonists of this invention. The antagonists also may be entrapped in microcapsules prepared, for example, by coacervation techniques or by interfacial polymerization (for example, hydroxymethylcellulose or gelatin-microcapsules and poly-[methylmethacylate) microcapsules, respectively), in colloidal drug delivery systems (for example, liposomes, albumin microspheres, microemulsions, nano-particles and nanocapsules), or in macroemulsions. Such techniques are disclosed in Remington's *Pharmaceutical Sciences*, 16th edition, Osol, A., ed., 1980).

In general, the formulations of the subject invention can contain other components in amounts not detracting from the preparation of stable forms and in amounts suitable for effective, safe pharmaceutical administration. For example, other pharmaceutically acceptable excipients well known to those skilled in the art can form a part of the subject compositions. These include, for example, salts, various bulking agents, additional buffering agents, chelating agents, antioxidants, cosolvents and the like; specific examples of these include tris-(hydroxymethyl)aminomethane salts ("Tris buffer"), and disodium edetate.

IgE levels are typically assayed by standard ELISA techniques well known in the art. Typically, IgE levels are undetectable by this technique below about 3 ng/ml.

Further details of the invention can be found in the following examples, which further define the scope of the invention. All references cited herein are expressly incorporated by reference in their entirety.

C. EXAMPLES

The role of IgE antibody production on schistosomiasis in naive mice was investigated in these studies. Anti-IgE mAb treatment, which reduced serum IgE to undetectable levels throughout the course of the infection, led to a significant reduction in both the number of adult worms and the number of eggs produced. Further, these anti-IgE mAb-treated mice also showed reduced hepatosplenomegaly. Taken together, these findings indicate that IgE production following *S. mansoni* infection in naive mice is an immunopathological consequence of the host-parasite interaction rather than a protective immune response.

1. Serum IgE Levels

In these studies, IgE was directly eliminated using a monoclonal anti-IgE antibody. Normal BALB/c mice were infected with *Schistosoma mansoni* cercariae and treated weekly with a total of 400 µg of anti-IgE mAb. This high dose treatment reduced serum IgE to undetectable levels during the eight week course of the infection (FIG. 1). A second group of mice treated with a lower dose of anti-IgE mAb weekly (240 µg/total anti-IgE mAb) had measurable IgE responses (less than 50 µg/ml) during the last two weeks of the infection. These levels were markedly reduced compared to infected mice treated with the isotype control antibody (Ab) which exhibited typically high serum IgE levels (240 µg/ml) by the eighth week of infection.

In agreement with previous reports (Sher, A. et al., *J. Immun.* 145:3911–3916 (1990)), significantly decreasing serum IgE levels, but not reducing to undetectable levels, had little effect on either parasite burden or fecundity (Table 1). In contrast, infected mice which had undetectable IgE levels as a result of treatment with the "high dose" of anti-IgE mAb had a significant reduction in the number of adult worms and the number of eggs produced, as compared to the control group.

TABLE 1

Effect of anti-IgE on egg-laying by S. mansoni worms in vivo

| Treatment | Control Ab (400 μg) | Anti-IgE (400 μg) | Anti-IgE (240 μg) |
|---|---|---|---|
| Number of adult worms | 41 ± 10 | 20 ± 2$^\varepsilon$ | 42 ± 10 |
| Total number of eggs/liver | 27061 ± 1128 | 5557 ± 1595$^\varepsilon$ | 23369 ± 4927 |
| Mean number eggs/adult | 656 ± 162 | 268 ± 72$^\varepsilon$ | 556 ± 69 |

Mice were killed by intraperitoneal injection of 15 mg sodium barbital and 30 units of heparin in 0.25 ml PBS. Adult worms were recovered by perfusion of the portal venous systezn (Amiri, P. et al., Nature 356:604–607 (1992)). Numbers reported are the mean number (n = 7–12/group) of worms per mouse ± standard deviation. To quantify parasite eggs in the liver, livers were homogenized for 20–30 seconds in 25 ml 1% trypsin in PBS. The mixture was incubated at room temperature for 3–4 hour, resuspended, then 20 μl samples removed for microscopic evaluation. The results are reported as the mean total egg number of ten independently counted samples per liver ± standard deviation.
$^\varepsilon$denotes significance at $p < .05$ as determined by analysis of variance; comparisons were performed using the Student-Newman-Keul Test.

2. Effects on Spleen and Liver

In the high dose (400 μg) mAb treated mice the overall cellular inflammatory reaction as measured by increases in the spleen (FIG. 2A) and liver (FIG. 2B) weight, was diminished by approximately 50% when compared to control IgG treated mice, presumably due to a decrease in egg production. Interestingly, mice that produced IgE only during the last two weeks of the infection (240 μg (low dose)) had equivalent numbers of eggs and equivalent increases in organ weight as the IgG treated animals. This finding implies a relationship between IgE synthesis in response to egg production and the ensuing cellular infiltration into the spleen and liver. Similarly, SJA/9 mice, which are genetically deficient in IgE, show a reduced granulomatous response to S. japonium eggs, again suggesting that IgE acts to amplify granuloma formation (Owhashi, M. et al., Int. Arch. Allergy. Appl. Immunol. 90:310–12 (1989)).

3. Effect on Egg Production

Figure 3A:
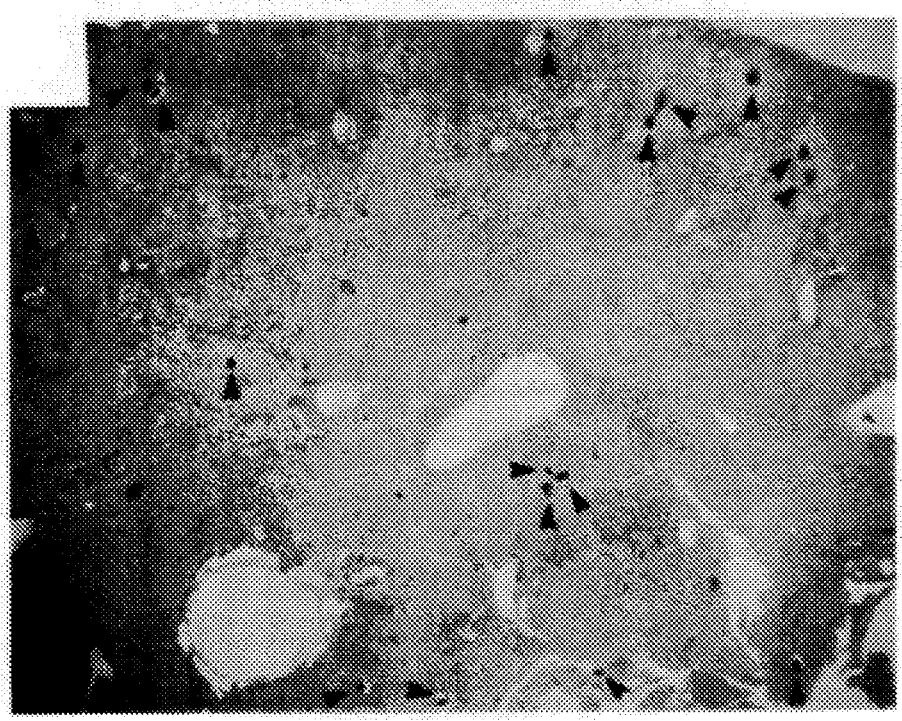
Figure 3B:
Figure 3C:
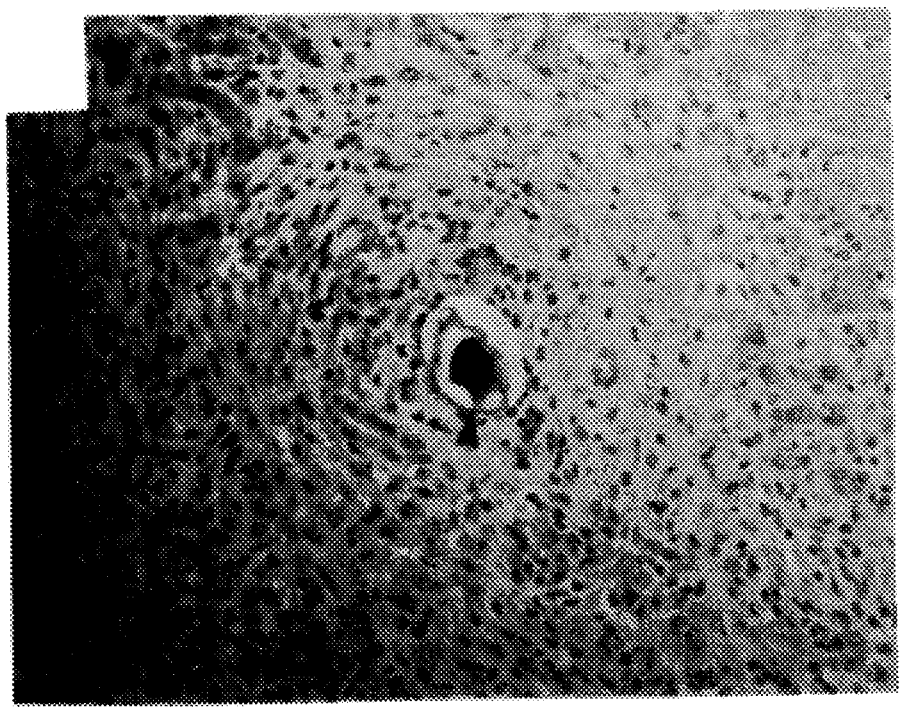
Figure 3D:
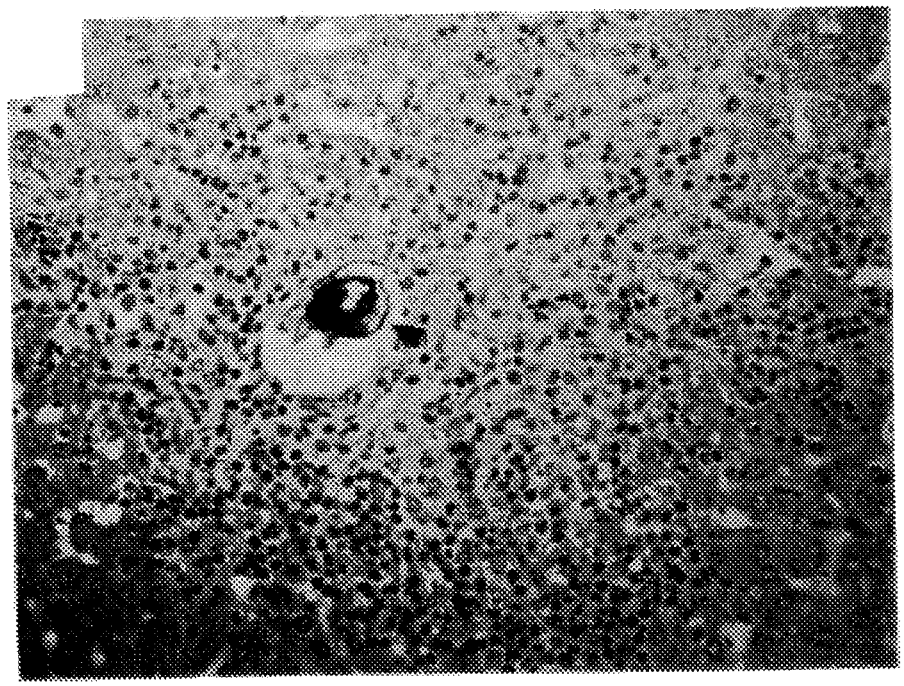

The key pathological event in schistosomiasis is chronic inflammation, characterized by granuloma formation around schistosome eggs trapped in the portal venules of the liver (Cheerer, A. W. et al., Am. J. Trop. Med. Hyg. 40:60–71 (1989)); Olds, G. R. et al., J. Infect. Dis. 159:798–901 (1989); Prakash, S. et al., J. Immun. 144:317–322 (1990)). Histopathological examination of the infected animals revealed that organ size correlated with the tissue inflammatory response (FIG. 3A). Due to the decreased numbers of eggs, there were marked reductions in the number of granulomas in the livers of the high dose anti-IgE mAb treated mice (FIG. 3B). Overall, the cellularity of the granulomas was not appreciably altered. Well-developed granulomas with numerous macrophages and eosinophils were observed in both groups of anti-IgE treated infected mice and IgG treated controls. However, the high dose treatment group did show decreased granuloma associated fibrosis (FIGS. 3C,D).

4. Effect on Serum IL-4

In addition to eliciting a potent inflammatory response, schistosome eggs are a powerful stimulus for clonal expansion and activation of the $T_{H2}$ subclass of CD4$^+$ T cells (Pearce, E.J. et al., J. Exp. Med. 173:159–166 (1992); Grzych, J. M. et al., Immun. 146:1322–1327 (1991)). $T_{H2}$ cells release specific cytokines, including interleukin 4 (IL-4) (Mosmann, T. F. et al., Ann. Rev. Immun. 7:145–173 (1989), which acts as a switch factor for IgE and IgG$_1$ (Stavnezer, J. et al., Proc. Natl. Acad. Sci. USA 85:7704–7708 (1988)). In these experiments, serum IL-4 rose to detectable levels during the seventh and eighth weeks of infection in control antibody treated mice (FIG. 4), coinciding with egg production (Vella, A. T. et al., J. Immun. 148:2283–2290 (1992)). However, in the sera of infected mice treated with anti-IgE mAb there was no similar spike of IL-4 (FIG. 4), indicating that complete suppression of IgE resulted in decreased $T_{H2}$ activity as measured by IL-4 production. Without being limited to any one particular theory, these findings suggest that in addition to IL-4 directing IgE synthesis, IgE may feedback to amplify IL-4 secretion, thereby modulating its own production.

The participation of IL-4 in anti-parasite effector function has been investigated using anti-IL-4 antibodies in a vaccinated mouse model (Sher, A., et al., J. Immun. 145:3911–3916 (1990)). Although this treatment reduced serum IgE along with IL-4, it failed to alter immunity against Schistosoma mansoni in the mouse. In contrast, the experiments presented here unexpectedly demonstrate that complete (as indicated by reducing IgE levels to undetectable), rather than partial, elimination of serum IgE along with IL-4 had favorable effects on immunity to parasites in a naive murine host. Without being limited to any one particular theory, it is still possible that locally produced IL-4, which promotes T cell growth (Kurt-Jones, E. A. et al., J. Exp. Med. 166:1774–1787 (1987); Fernandez-Botran, R. et al., J. Exp. Med. 168:543–558 (1988)) and development (Tepper, R. I. et al., Cell 62:457–467 (1990)) contributed to the reduction in worm burden and fecundity.

In an alternative theory, IgE may play a role in protecting the parasite from an effective anti-parasite response. Since the elimination of IgE also resulted in profound suppression of IL-4, it is possible that this immunoglobulin isotype may skew the $T_H$ response to schistosome eggs. Previous reports have established an association with $T_{H1}$ stimulation and protection against adult worms versus $T_{H2}$ stimulation and egg-induced immunopathology (Scott, P. et al., Immun. Rev. 112:161–182 (1989)). Indeed, it has been suggested that, in mice, the $T_{H2}$ response to schistosoma eggs results in both immunopathogenesis and down-regulation of the $T_{H1}$ response (Vella, A. et al., J. Immun. 148:2283–2290 (1992)). Thus, elimination of IgE via anti-IgE mAb treatment may simply shift the balance from a $T_{H2}$ response towards a $T_{H1}$ response. The mediators and cytokines produced by these $T_{H1}$ cells may be more effective in controlling the parasite infection (James S. L. et al., Curr. Top. Microbiology Immunol. 21:31–39 (1990)).

5. Effect on Serum IFN-α

To further investigate the relative contribution of $T_{H1}$ and $T_{H2}$-derived cytokines in this system, sera were also assayed for IFN-α, a $T_{H1}$ product which has been shown to confer protective immunity to S. mansoni (Pancre, V. H. et al., Cell Immunol. 125:58–64 (1990)). Although the ELISA used was sensitive to 15 pg/ml, no circulating IFN-α was detected in any of the serum samples collected during the eight week course of Schistosoma infection (data not shown). However, IFN-α levels were measurable in the supernatants of concanavalin A stimulated spleen cells taken from uninfected mice and from infected mice treated with anti-IgE or control antibody. In agreement with published findings (Sher, A. R. et al., Proc. Natl. Acad. Sci. USA 87:616–65 (1990)), IFN-α levels in the cultures were greatly suppressed eight weeks after infection (560 ng/ml uninfected mice versus 18 ng/ml infected mice). Interestingly, treatment with the anti-IgE antibody partially reversed this suppression, elevating IFN-α to 67 ng/ml in the supernatants of splenocytes from infected mice. These results suggest that $T_{H1}$ cells, as inferred from the detection of IFN-α, are more abundant following antibody treatment and can contribute in part to the improved immune response against the parasite.

6. Effect on CD23 Expression

In an effort to identify other events associated with anti-IgE treatment of *Schistosoma* infected mice, splenic lymphoid cells were evaluated for differential surface marker expression eight weeks after infection with cercariae. IL-4 is known to increase cell surface expression of the low affinity receptor for IgE (FcεRII), CD23 (Kikutani, H. et al., *Cell* 47:657–665 (1986)). Examination of CD23 expression on splenic CD45R+ B cells revealed that CD23 expression was enhanced in response to *Schistosoma* infection but was suppressed back to the level of expression seen in uninfected mice following treatment with anti-IgE mAb (FIG. 5). The lack of enhancement in CD23 expression is consistent with the absence of detectable IL-4 levels in the anti-IgE treated mice. Furthermore, FcεRII can act quite efficiently in the capture and presentation of antigens associated with IgE (Kehry, M. R. et al., *Proc. Natl. Acad. Sci. U.S.A.* 86:7556–7560 (1989)) and may preferentially present antigen for IgE ($T_{H2}$) responses. Since the presentation of certain parasite antigens has been associated with either $T_{H1}$ or $T_{H2}$ cell development, one of the IgE feedback mechanisms may be linked to the presentation of IgE bound antigen(s) which stimulate $T_{H2}$ cell development. The IgE/FcεRII interaction in vitro has been shown to effect immunoglobulin isotype selection and to stimulate B cell proliferation (Scott, P., et al., *Immun. Rev.* 112:161–182 (1989)). Without being limited to any one particular theory, interference with IgE synthesis by blocking IgE interactions with CD23-bearing B cells could explain the ability of relatively low doses (100 μg/week) of the anti-IgE antibody to totally eliminate the very high IgE levels (240 μg/ml) normally stimulated by this parasite.

We claim:

1. A method of treating a patient having a parasite infection which parasite infection is associated with elevated IgE levels comprising administering an amount of an IgE antagonist to the patient, which is sufficient to reduce the patient's IgE levels such that they are undetectable during the course of treatment.

2. The method of claim 1 wherein the parasite is a helminth.

3. The method of claim 2 wherein the parasite is *Schistosoma*.

4. The method of claim 1 wherein the IgE antagonist is selected from the group consisting of an anti-IgE antibody, an anti-IgE receptor antibody, an IgE receptor, an IgE receptor variant, an IgE receptor ligand, or an IgE variant.

5. The method of claim 4, wherein the anti-IgE antibody and anti-IgE receptor antibody are humanized.

6. The method of claim 1 wherein the antagonist comprises an anti-IgE or anti-IgE receptor antibody fragment which antagonizes IgE.

7. The method of claim 1 wherein the antagonist comprises an anti-IgE or anti-IgE receptor antibody, and said antibody is of the IgA, IgG, IgE, or IgM class.

8. The method of claim 1, wherein the parasite is a metazoan.

9. The method of claim 1, wherein the patient's IgE levels are reduced during treatment such that they are below about 3 ng/ml.

10. A method of reducing the number of adult worms or eggs in a patient infected by a parasite which parasite infection is associated with elevated IgE levels comprising administering an amount of an IgE antagonist to the patient, which is sufficient to reduce the patient's IgE levels such that they are undetectable during the course of treatment.

11. The method of claim 10 wherein the parasite is a helminth.

12. The method of claim 11 wherein the parasite is *Schistosoma*.

13. The method of claim 10 wherein the IgE antagonist is selected from the group consisting of an anti-IgE antibody, an anti-IgE receptor antibody, an IgE receptor, an IgE receptor variant, an IgE receptor ligand, or an IgE variant.

14. The method of claim 13, wherein the anti-IgE antibody and anti-IgE receptor antibody are humanized.

15. The method of claim 10 wherein the IgE antagonist comprises an anti-IgE or anti-IgE receptor antibody fragment which antagonizes IgE.

16. The method of claim 10 wherein the IgE antagonist comprises an anti-IgE or anti-IgE receptor antibody, and said antibody is of the IgA, IgG, IgE, or IgM class.

17. The method of claim 10, wherein the parasite is a metazoan.

18. The method of claim 10, wherein the patient's IgE levels are reduced during treatment such that they are below about 3 ng/ml.

19. A method of reducing hepatosplenomegaly in a patient infected by a parasite which parasite infection is associated with elevated IgE levels comprising administering an amount of an IgE antagonist to the patient, which is sufficient to reduce the patient's levels such that they are undetectable during the course of treatment.

20. The method of claim 19 wherein the parasite is a helminth.

21. The method of claim 20 wherein the parasite is *Schistosoma*.

22. The method of claim 19 wherein the IgE antagonist is selected from the group consisting of an anti-IgE antibody, an anti-IgE receptor antibody, an IgE receptor, an IgE receptor variant, an IgE receptor ligand, or an IgE variant.

23. The method of claim 22, wherein the anti-IgE antibody and anti-IgE receptor antibody are humanized.

24. The method of claim 19 wherein the IgE antagonist comprises an anti-IgE or anti-IgE receptor antibody fragment which antagonizes IgE.

25. The method of claim 19 wherein the IgE antagonist comprises an anti-IgE or anti-IgE receptor antibody, and said antibody is of the IgA, IgG, IgE, or IgM class.

26. The method of claim 19, wherein the parasite is a metazoan.

27. The method of claim 19, wherein the patient's IgE levels are reduced during treatment such that they are below about 3 ng/ml.

28. A method of treating a patient having a parasite infection which is caused by a helminth comprising administering to said patient an amount of an IgE antagonist sufficient to reduce hepatosplenomegaly and/or to reduce the number of helminthic worms or eggs.

29. The method of claim 28 wherein the helminth is *Schistosma*.

\* \* \* \* \*